United States Patent [19]

Johnstone

[11] Patent Number: 5,538,502
[45] Date of Patent: Jul. 23, 1996

[54] SURGICAL CHEST DRESSING

[75] Inventor: Haidee M. Johnstone, Minneapolis, Minn.

[73] Assignee: Golda, Inc., Beachwood, Ohio

[21] Appl. No.: 364,123

[22] Filed: Dec. 27, 1994

[51] Int. Cl.⁶ ............................................. A61F 13/00
[52] U.S. Cl. ......................... 602/79; 602/19; 602/61; 450/1; 450/63
[58] Field of Search ............................ 602/19, 79, 58, 602/75, 60, 61; 450/1, 58, 63, 65, 76

[56] References Cited

U.S. PATENT DOCUMENTS

| | | |
|---|---|---|
| 2,443,127 | 6/1948 | Abeles . |
| 2,596,275 | 5/1952 | Muller .................................. 602/79 |
| 2,662,522 | 12/1953 | Muller . |
| 3,486,501 | 12/1969 | Erickson et al. ..................... 602/71 |
| 3,561,442 | 2/1971 | Goswitz . |
| 3,568,681 | 3/1971 | Comollo . |
| 3,628,539 | 12/1971 | Fredricks . |
| 3,957,057 | 5/1976 | Farino . |
| 3,968,803 | 7/1976 | Hyman ................................. 602/79 |
| 4,475,543 | 10/1984 | Brooks et al. ....................... 602/19 |
| 5,152,741 | 10/1992 | Farino ................................. 602/79 |
| 5,188,585 | 2/1993 | Peters ................................. 602/19 |

FOREIGN PATENT DOCUMENTS 2279344  2/1976  France .

*Primary Examiner*—Richard J. Apley
*Assistant Examiner*—Kim M. Lee
*Attorney, Agent, or Firm*—Vickers Daniels & Young

[57] ABSTRACT

A surgical chest dressing is constructed of a band of stretchable material having a pair of panels of non-stretchable material attached thereto, the non-stretchable panels biasing the side and breast tissue of a patient inwardly toward a sutured incision in the center of a patient's chest to support and substantially immobilize the patient's side and breast tissue and to minimize stress on the sutured incision.

24 Claims, 7 Drawing Sheets

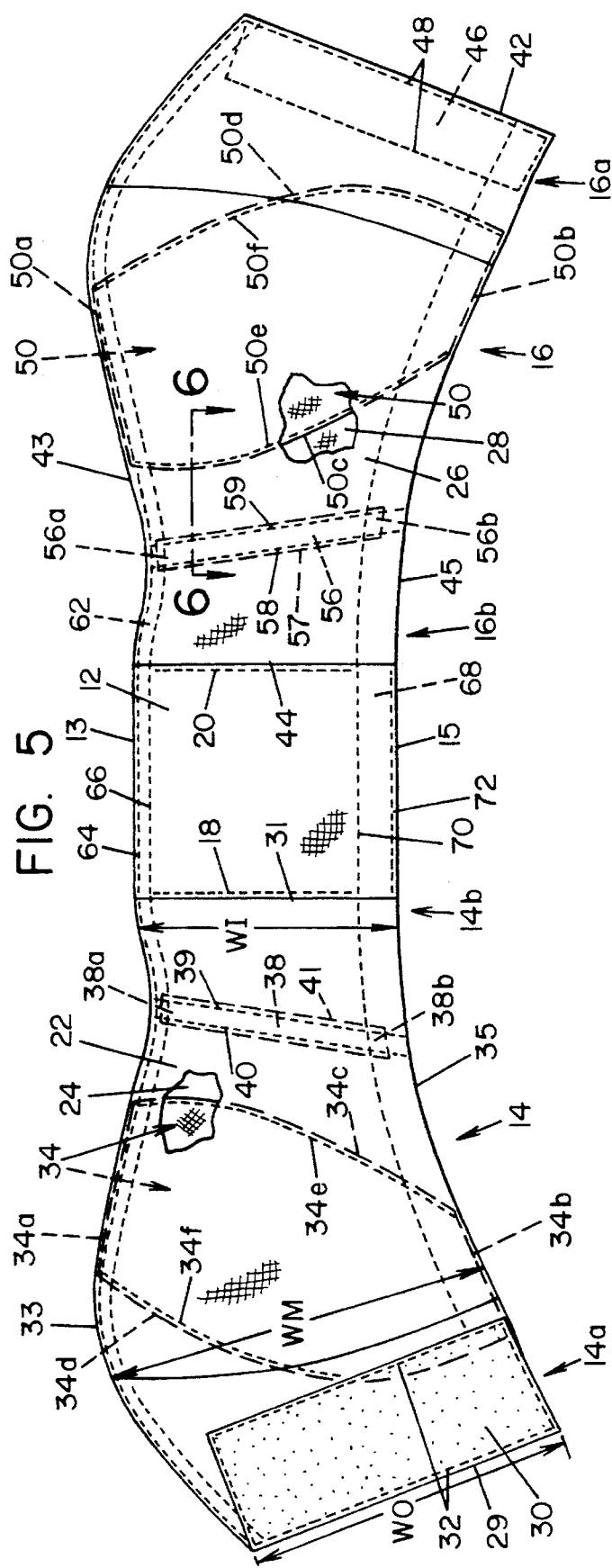

SURGICAL CHEST DRESSING

The subject invention is directed toward a surgical chest dressing and more particularly to a surgical chest dressing for minimizing stress on post-operative incisions.

BACKGROUND OF THE INVENTION

After a chest operation such as open heart surgery, a patient is normally bandaged with an absorbent material over an incision and wrapped with an elastic band or dressing of the type disclosed in U.S. Pat. No. 3,968,803 to Hyman or a stretchable chest dressing of the type described in U.S. Pat. No. 5,152,741 to Farnio. Both the Hyman and Farnio patents are owned by a common assignee with this application and the disclosures of each are incorporated herein by reference.

Open heart surgery or other surgery where the chest cavity is opened involves making an incision over the sternum or breastbone beginning near the patient's throat and extending downwardly six to ten inches through skin and the pectoral muscles which are attached to the sternum. Next, the ligaments which hold the ribs to the sternum must be severed so that the ribs over the patient's heart can be pried back to expose the heart and lungs. The surgery is extremely painful and ribs, sternum and muscles must be adequately supported after surgery to allow the region to heal. The healing process may be complicated if the individual is obese or is a woman having large breasts. This is because the breasts or excess fatty tissue of a patient lying in a supine position tend to fall away from the center of the patient's chest and toward the patient's sides. This, in turn, stresses the sutures along the sternum and causes pain as the moving flesh pulls at the patient's injured ribs. Thus, recovery for such patients may be more painful and lengthy than it would if the breasts or breast tissue were immobilized.

In the past, rigid splints were used to provide support for chest tissue and, generally, to immobilize the chest area while an incision healed. Such splints caused breathing difficulties, were uncomfortable and therefore unacceptable. An improved dressing is disclosed in U.S. Pat. No. 5,152,741 to Farnio and is designed to provide support for injured tissue on the side of a patient's body which is present after a mastectomy. Such dressings may be used after any type of chest surgery, but are not well suited for relieving the stress on incisions which result from open chest surgery and the like, because they do not adequately restrain the breasts and breast tissue. If applied exceptionally tightly in an attempt to reduce the mobility of the breast tissue, flesh tends to bunch beneath the patient's arms and the patient's breasts are uncomfortably flattened. This is uncomfortable and has been found unacceptable.

Furthermore, prior dressings of the type disclosed in Farnio generally utilize straps to hold the dressing in place. These dressings are often slightly cupped in the front to accommodate a breast or a cushioning layer of bandage over a post-mastectomy incision. These dressings thus resembled brasseries and are considered undesirable by male patients.

SUMMARY OF THE INVENTION

The present invention overcomes these problems and others by providing a surgical chest dressing designed to hold the patient's breasts relatively immobile while pressing them slightly toward the line of the incision.

In accordance with the invention, a surgical chest dressing is formed of a chest encircling flexible band of stretchable material having two substantially non-stretchable portions included therein and two free ends which are attachable to one another. The stretchable portions conform generally to the wearer's body while the non-stretchable portions position the patient's breasts so as not to stress an incision centrally located therebetween.

Also in accordance with the invention, the chest encircling flexible band is made from one or preferably two plies of stretchable material. This band may be continuous or include a panel of elastic material in the middle thereof to allow individuals of different sizes to use a particular size dressing. This elastic panel also allows the dressing to expand as the patient breathes while maintaining a constant closing pressure on the incision. Because the elastic is located on the patient's back, away from any incision, the problems seen in the prior art when elastic dressings were used are avoided. Attached to or between the plies of stretchable material are two panels of flexible, substantially non-stretchable pieces of material which will be located in proximity to the patient's breasts when the dressing is in place. The ends of the band may be attached to one another using any suitable fastener arrangement such as a Velcro fastener assembly.

It is therefore a principal object of the present invention to provide a surgical chest dressing for patients who have undergone chest surgery.

It is another object of the present invention to provide a surgical chest dressing which is comfortable to wear.

It is a further object of the present invention to provide a surgical chest dressing which minimizes stress on surgical incisions.

It is another object of the present invention to provide a chest dressing which maintains an even closing pressure across the incision along the entire length of the incision.

It is still a further object of the present invention to provide a chest dressing which does not fold and bunch uncomfortably beneath the wearer's arms.

It is yet another object of the present invention to provide a surgical chest dressing which substantially immobilizes the breasts of the wearer.

It is yet a further object of the present invention to provide a surgical chest dressing which is acceptable to both male and female patients.

It is still another object of the present invention to provide a surgical chest dressing which immobilizes the breasts of the wearer without causing excess flesh beneath the wearer's arms to bulge out.

It is still a further object of the present invention to provide a surgical chest dressing made from stretchable material which allows a patient to cough and breathe deeply without stressing an incision in the patient's chest.

It is yet another object of the present invention to provide a surgical chest dressing for biasing the breast tissue of a person away from a person's sides and the tissue adjacent a person's armpit toward the person's front.

BRIEF DESCRIPTION OF THE DRAWINGS

FIG. 5 is a plan view of the outer side of the surgical chest dressing shown in FIG. 1 but without the shoulder straps;

FIG. 6 is a sectional plan view taken through line 6—6 in FIG. 5 showing the interior structure of the chest dressing of the invention;

DETAILED DESCRIPTION OF PREFERRED EMBODIMENTS

Figure 1:
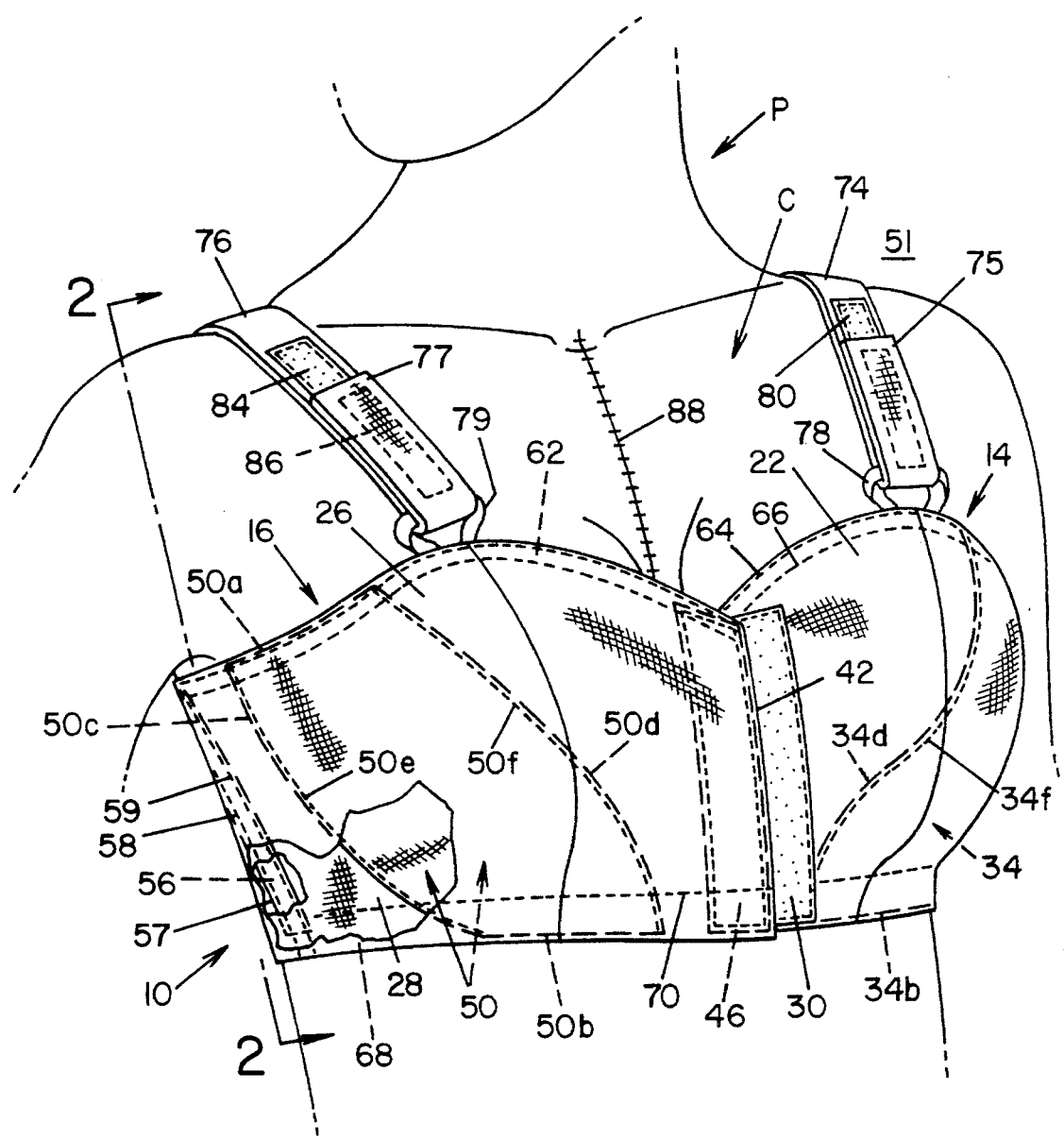
FIG. 1 is a perspective view showing a patient wearing a surgical chest dressing in accordance with the invention and which dressing includes optional shoulder straps.
Figure 4:
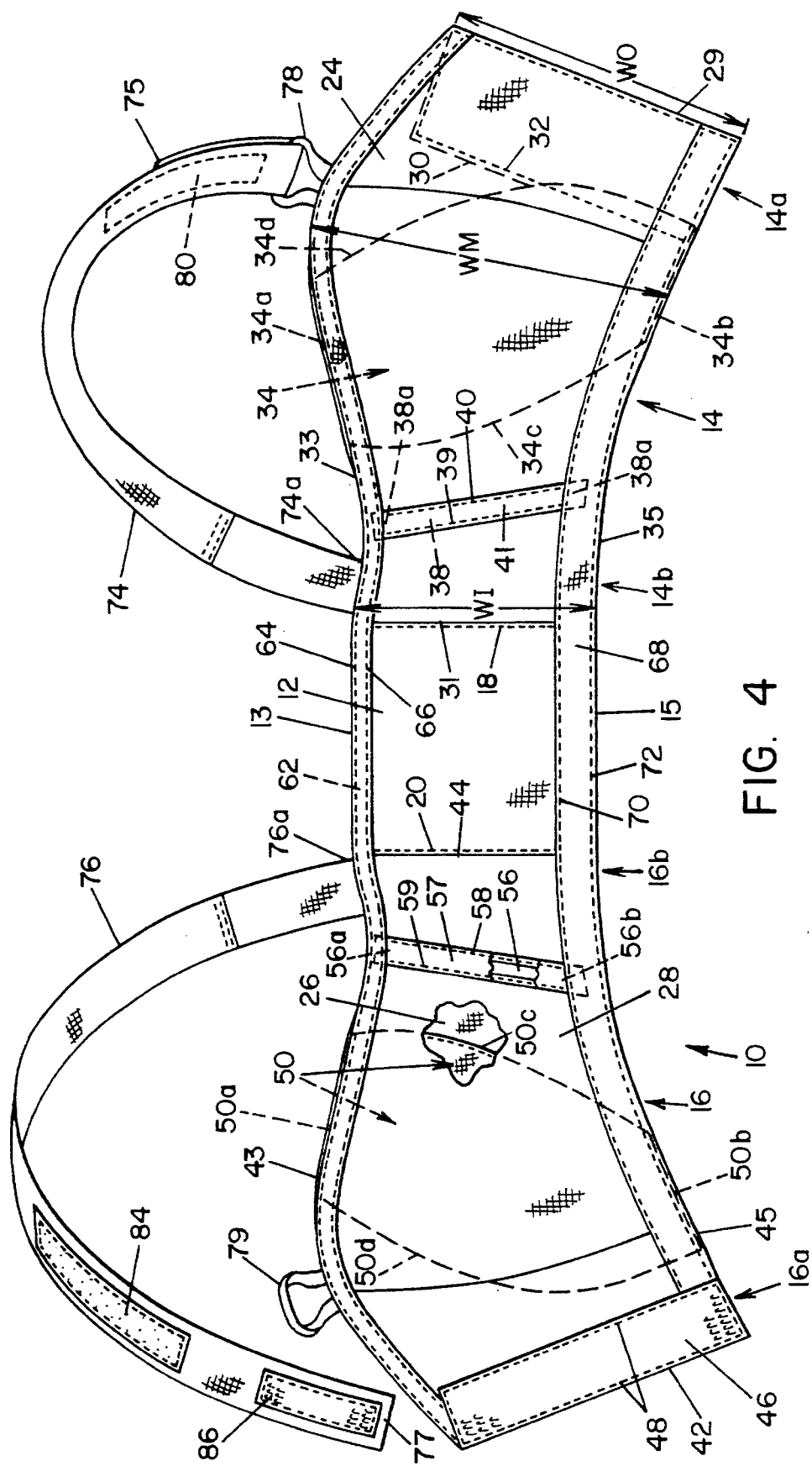
FIG. 4 is a plan view of the inner side of the surgical chest dressing shown in FIG. 1.

Referring now to the drawings wherein the showings are for the purpose of illustrating preferred embodiments of the invention only and not for the purpose of limiting same, FIG. 1 shows a surgical chest dressing designated generally by the number 10 wrapped around the chest region C of a person P. As shown in FIGS. 1, 4 and 5, dressing 10 comprises an elastic central panel 12 having a top edge 13 and a bottom edge 15 joined to a left dressing half 14 by stitching 18 and to a right dressing half 16 by stitching 20. Left panel half 14 includes an outer end 14a having an outer edge 29, an inner end 14b having an inner edge 31, a top edge 33 and a bottom edge 35. Right dressing half 16 includes an outer end 16a having an outer edge 42, an inner end 16b having an inner edge 44, a top edge 43 and a bottom edge 45. The terms "left" and "right" are used to describe the orientation of dressing halves 14, 16 as shown in FIG. 5. When dressing 10 is placed on a patient, left dressing half 14 will overlay the left side of the patient's chest and right dressing half 16 will overlay the right side of a patient's chest; however, a person looking from the front at a person wearing dressing 10, as in FIG. 1, will see these directions as reversed. Left dressing half 14 and right dressing half 16 are substantially identical to one another except with respect to the fasteners used on the respective halves which will be described in greater detail hereinafter. Left dressing half 14 comprises two plys of a stretchable material, an outer ply 22 and an inner ply 24, and right dressing half 16 comprises an outer ply 26 and an inner ply 28. The material of plys 22, 24 26 and 28 may, for example, be 100% nylon jersey. Outer end 29 of left dressing half 14 is provided with a panel 30 of the loop component of a Velcro fastener which is attached to plys 22 and 24 of left panel half 14 by stitching 32. A panel 34 of non-stretchable material such as acetate tricot covered with latex foam is disposed between outer ply 22 and inner ply 24, as explained more fully hereinafter, and a stay cover 41 overlies inner ply 24 and is attached to plys 22 and 24 by stitching 39 and 40 to hold a stay 38 in place. Stay 38 is preferably formed from a flexible strip of thin metal or a plastic.

Working from outer end 42 of right dressing half 16 toward inner edge 44 of right dressing half 16, dressing half 16 comprises a panel 46 of the hook component of a Velcro fastener fastened to plys 26 and 28 by stitching 48 such that the hooks on panel 46 will face toward the chest region C of a patient wearing dressing 10. Moving away from outer edge 42, right dressing half 16 next comprises a panel 50 of the same non-stretchable material as panel 34 disposed between outer ply 26 and inner ply 28 and fastened between plys 26 and 28 by stitching as described hereinafter. A stay cover 57 is sewn to inner ply 28 with stitching 58 and stitching 59 to hold a stay 56 in place. The inner edge 44 of panel half 16 is fastened to elastic panel 12 by a row of stitching 20. FIG. 6 is a cross section of a portion of dressing 10 taken through stay 56 and a portion of panel 50 showing how these parts are fastened within the plys of dressing 10.

Left dressing half 14 has an outer width WO along outer edge 29, an inner width WI along inner edge 31, and a maximum width WM located approximately one-third of the distance inwardly from outer edge 29. Width WO is greater than width WI. Bottom edge 35 of left dressing half 14 is slightly concave between outer edge 29 and inner edge 31. The width of dressing 10 across left dressing half 14 increases gradually inwardly from outer edge 29 as top edge 33 of dressing half 14 curves away from bottom edge 35 of dressing half 14 until the maximum width WM is reached at a point approximately one-third of the way in from edge 29. From the point at which width WM is reached, top edge 33 slopes gradually back toward bottom edge 35 and the width of dressing 10 decreases until the width WI is reached shortly before top edge 33 meets inner edge 31. Left panel half 14 and right panel half 16 are identical except for the different Velcro fastener components 30 and 46.

A top strip of elastic material 62 runs from outer edge 29 of left dressing half 14 across top edge 33 of dressing half 14, across top edge 13 of panel 12, across top edge 43 of right dressing half 16 and terminates at outer edge 42 of dressing half 16. The top elastic strip is shown fastened in place by stitching 64 and 66 but a single row of zig zag stitching or other well known attachment methods could also be used. In a similar manner, a bottom elastic strip 68 runs from outer edge 29 of left dressing half 14 across bottom edge 35 of dressing half 14, across the bottom edge 15 of elastic panel 12, across bottom edge 45 of right panel half 16 and terminates at outer edge 42 of dressing half 16. Bottom strip 68 is shown fastened in place by stitching 70 and 72 but a single row of zig zag stitching or other well known attachment method could also be used.

Panel 34 of non-stretchable material has a top edge 34a, a bottom edge 34b an inner edge 34c inclined and curving toward elastic panel 12 and an outer edge 34d inclined and curving toward outer edge 29. Top edge 34a generally coincides with the corresponding portion of top edge 13 of left dressing half 14 in the region where the width is decreasing from width WM to width WI. Bottom edge 34b of panel 34 coincides with the corresponding portion of bottom edge 33 of dressing half 14 but is disposed closer to outer edge 29 than is top edge 34a. Stay 38 is located between panel 34 and inner edge 31 and extends from a point between stitching 64 and stitching 66 to a point between stitching 70 and stitching 72. Stay 38 is secured at its top end 38a by stitching 66 and at its bottom end 38b by stitching 70. Inner edge 34c of panel 34 is secured to panels 22 and 24 by a row of stitching 34e and outer edge 34d of panel 34 is secured in place by a row of stitching 34f while top edge 34a of panel 34 is held in place by stitching 64 and stitching 66 which runs along top elastic strip 62. Bottom edge 34b of panel 34 is held in place by stitching 70 and stitching 72 which also secures bottom elastic strip 68 to dressing 10. On right dressing half 16, stay 56 is secured at its top end 56a by stitching 66 and at its bottom end 56b by stitching 70. In a similar manner, panel 50 of non-stretchable material on right dressing half 16 includes a top edge 50a, a bottom edge 50b, an inner edge 50c inclined and curving toward elastic panel 12 and secured by stitching 50e and an outer edge 50d inclined and curving toward outer edge 42 and secured by stitching 50f. Top edge 50a is secured by stitching 64 and 66 while bottom edge 50b is secured by stitching 70 and 72.

When or if additional support is desired, shoulder straps may be used. In this respect, and as best seen in FIG. 4, a left strap 74 is attached to left dressing half 14 and a right strap 76 is attached to right dressing half 16. End 74a of strap 74 is attached to top edge 33 of dressing half 14 between plies 22 and 24 and near inner edge 31 by stitching 64 and 66. A loop 78 is attached to top edge 33 of dressing half 14 in the vicinity of the maximum width WM thereof and is also held in place between plies 22 and 24 by stitching 64 and 66. Strap 74 has an end 75 and panels of Velcro fastener components are affixed to strap 74 on one side of end 75 as designated generally by numeral 80 and which panels are cooperable to adjustably attach end 75 to loop 78. Similarly, end 76a of strap 76 is attached by stitching 62 and 64 to top edge 43 of dressing half 16 between plies 26 and 28 near inner edge 44, and a loop 79 is attached to top edge 43 of dressing half 16 between plies 26 and 28 in the vicinity of maximum width WM by stitching 62 and 64. Panels of Velcro fastener components 84 and 86 are attached to one side of strap 76 near end 77 thereof for adjustably attaching end 77 to loop 78.

Figure 2:
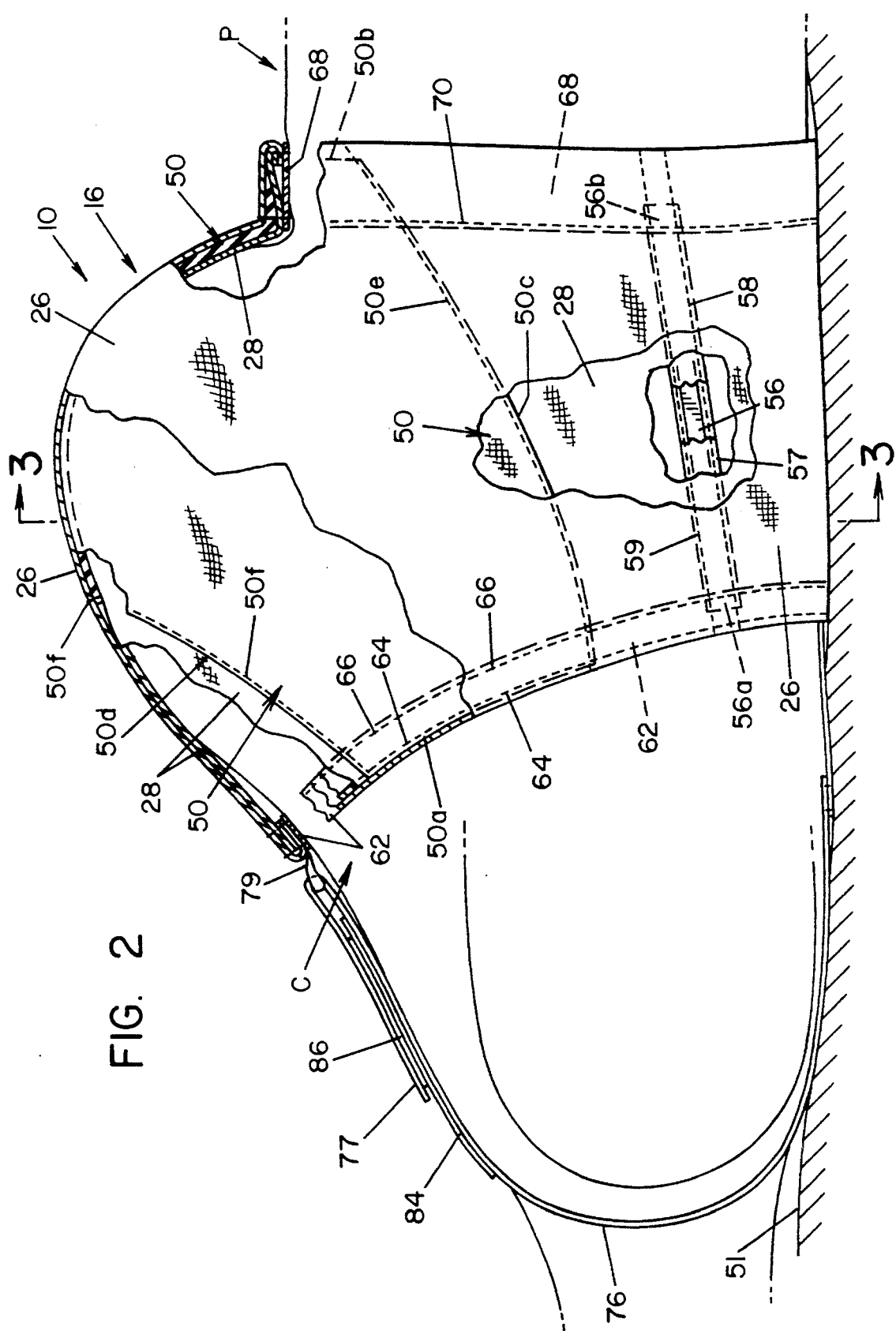
FIG. 2 is a side elevation view looking in the direction of line 2—2 in FIG. 1 and showing the side of the patient in FIG. 1 in a supine position.
Figure 3:
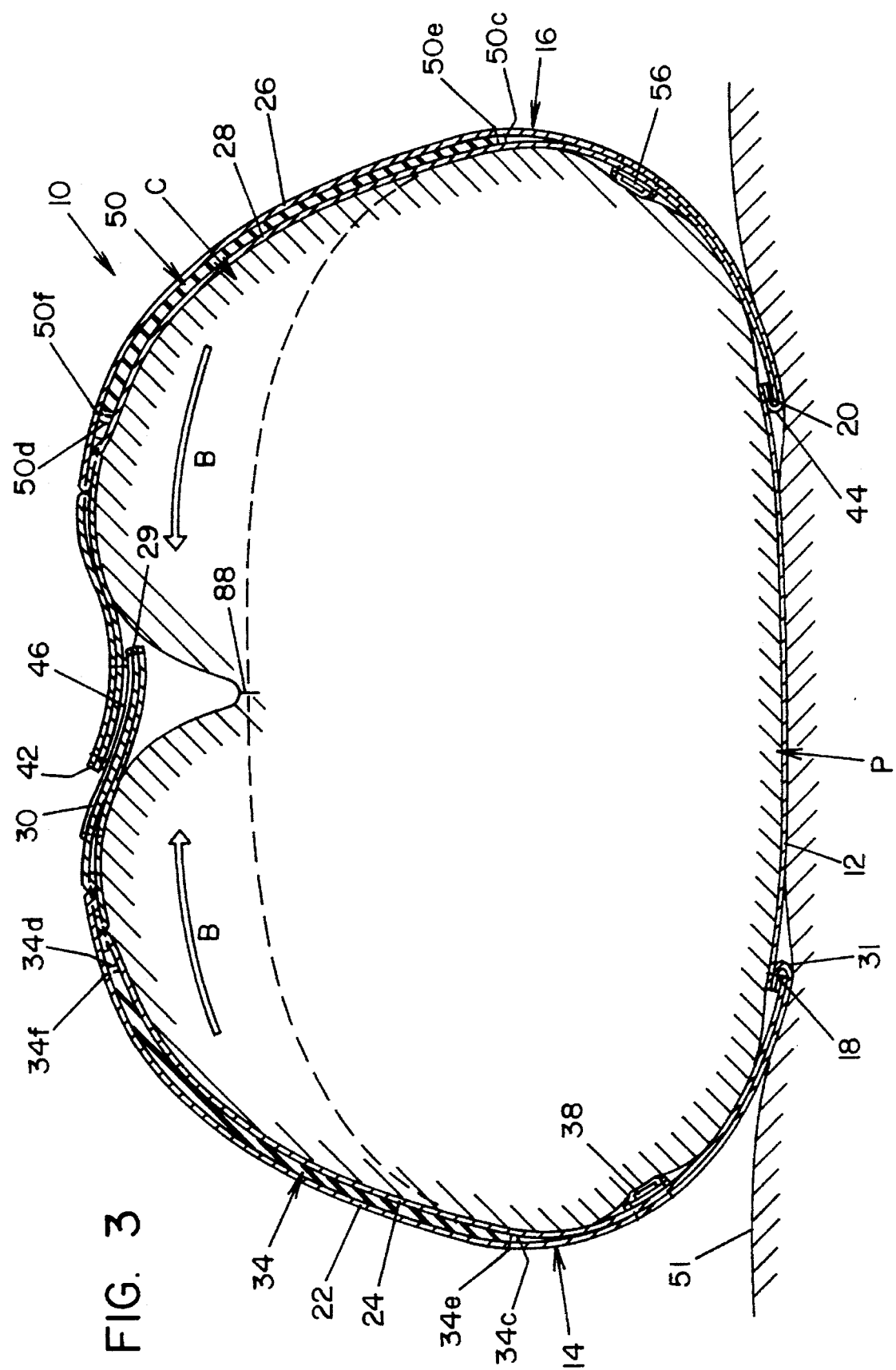
FIG. 3 is a sectional elevation view taken through line 3—3 in FIG. 2 showing the positioning of the breasts of the patient in FIG. 2 wearing the chest dressing of the subject invention.

To apply dressing 10 to a patient, as best seen in FIGS. 2 and 3, dressing 10 is laid flat on a horizontal surface 51, such as a bed, with inner plies 24 and 28 facing away from surface 51. A patient P is placed on dressing 10 in a supine position so that elastic panel 12 is generally centered from left to right across the patient's back and below the post-operative incision. In this position, outer edge 42 and part of right dressing half 16 will extend outwardly of the patient's right arm and outer edge 29 and a portion of left dressing half 14 will extend outwardly of the patient's left side. If the dressing has the optional shoulder straps, the straps are positioned so that left strap 74 extends upwardly from beneath the patient's left shoulder next to the left side of the patient's head and right shoulder strap 76 extends upwardly from beneath the patient's right shoulder next to the right side of the patient's head. Left and right dressing halves 14 and 16 and Velcro panels 30 and 46 thereof are brought beneath the patient's arms and across the patient's chest toward each other and toward incision 88. Panels 46 and 30 are pulled into an overlapping position and pressed together to fasten dressing 10 snugly about the patient's chest. If the dressing has shoulder straps, at this time left strap 74 is pulled over the patient's left shoulder, end 75 is inserted through loop 78, pulled snug, and folded over so that Velcro fastener 80 will hold the strap in this orientation. Right strap 76 is positioned and fastened in a similar manner by Velcro components 84 and 86. FIG. 1 shows dressing 10 having shoulder straps fastened in this manner.

Figure 7:
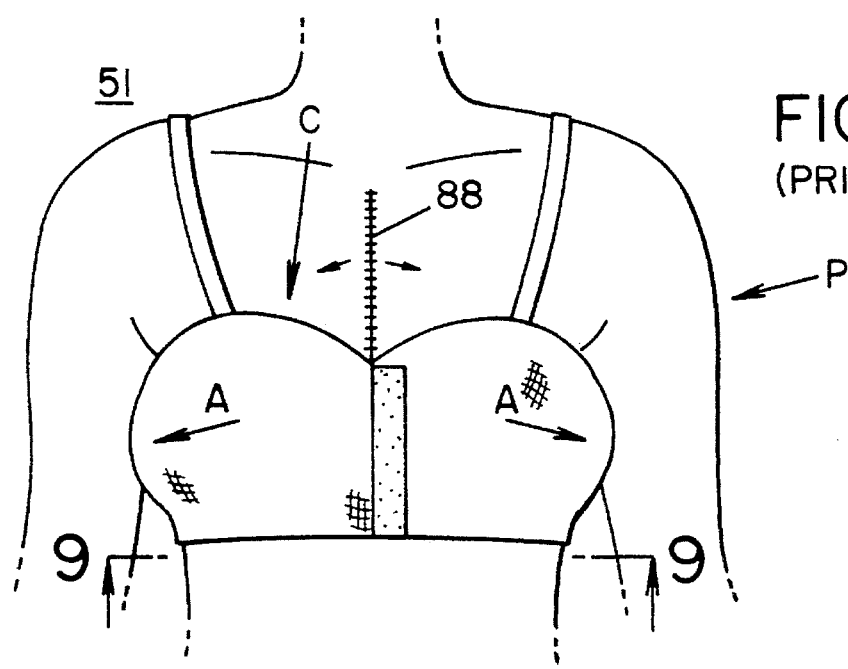
FIG. 7 is a plan view of a supine patient wearing a prior art dressing and showing how this dressing allows the patient's breasts to fall toward the sides of the patient's body.
Figure 8:
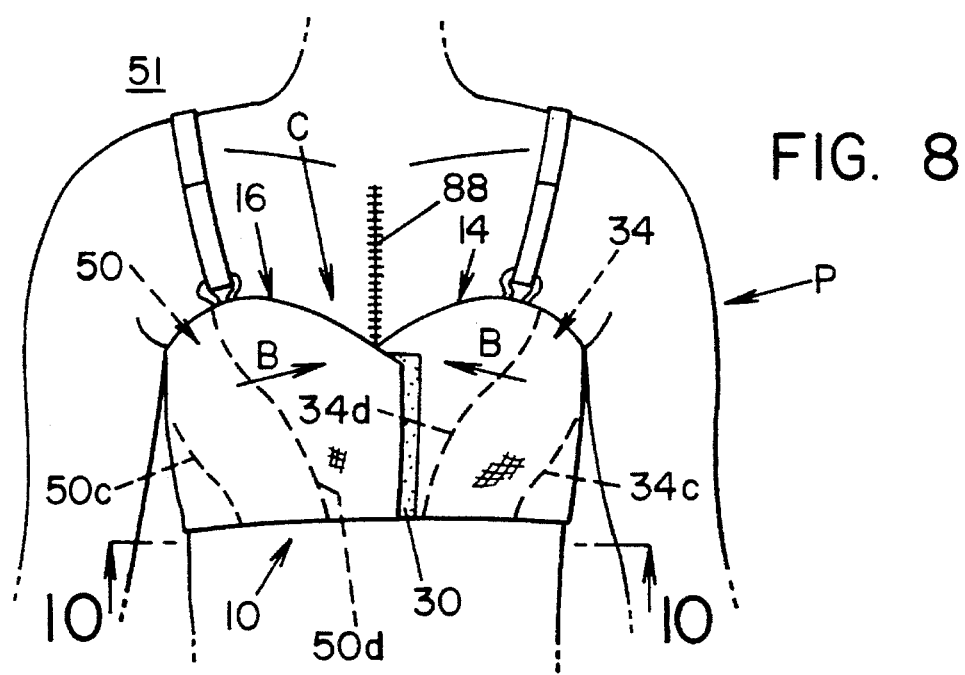
FIG. 8 is a plan view of a supine patient wearing a surgical chest dressing according to the invention and showing how the patient's breasts are biased toward one another by the dressing.
Figure 9:
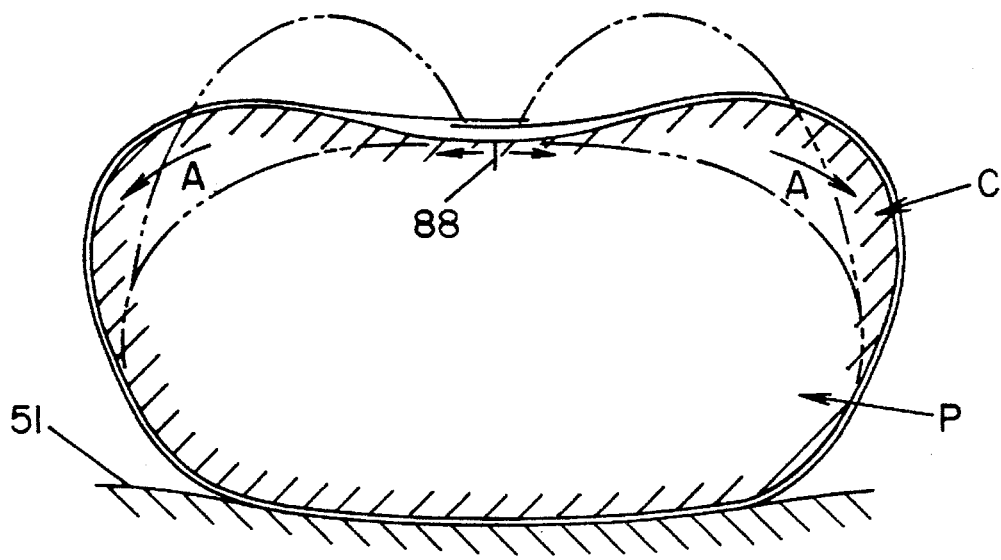
FIG. 9 is a sectional elevation view taken along line 9—9 of FIG. 7 showing how the breasts of a patient wearing a prior art dressing tend to stress an incision located between the patient's breasts.
Figure 10:
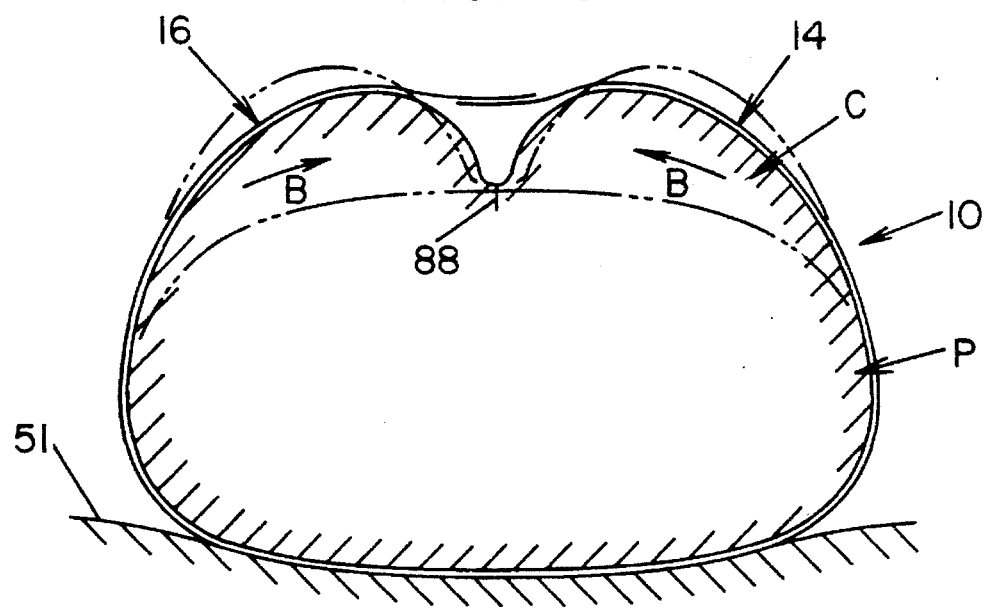
FIG. 10 is a sectional elevation view taken along line 10—10 of FIG. 8 showing how the subject invention prevents the breasts of a wearer from stressing an incision between the wearer's breasts.

The benefits of the invention will be appreciated from the illustrations in FIGS. 7 and 9 in comparison with FIGS. 2, 3, 8 and 10. As can be seen in FIGS. 7 and 9, prior art dressings do not provide adequate lateral support to keep the breasts of a patient in a supine position from falling toward the sides of the patient's body as shown by arrows A and thus placing stress on incision 88. This stress is not only painful for the patient but also can slow down the healing process with respect to incision 88 and can result in the incision not healing properly. As shown in FIGS. 2, 3, 8 and 10, however, dressing 10 advantageously biases the sides and breasts of the patient inwardly toward incision 88 as shown by arrows B to prevent incision 88 from being stressed in the foregoing manner. More particularly in this respect, in fastening left dressing half 14 to right dressing half 16, left dressing half 14 is first pulled between the patient's left arm and left side so that it is generally perpendicular to elastic panel 12, and right dressing half 16 is similarly oriented so that it is parallel to left half 14. The right and left halves are then pulled across the patient's chest toward incision 88 and are fastened together by Velcro components 30 and 46. As shown in FIGS. 2 and 3, this positions panels 34 and 50 along the corresponding side of the patient including the outer sides of the patient's breasts. In these positions of panels 34 and 50, the top, bottom, outer and inner edges thereof are positioned relative to the patient's body as shown in FIG. 2 with regard to panel 50. In this respect, top edge 50a of panel 50 extends along the patient's side and the upper area of the breast toward the patient's front while outer edge 50c extends along the side of the breast from top edge 50a to bottom elastic strip 68 and bottom edge 50b of the panel. Elastic strip 68 and the bottom edge portion of panel 50 are positioned beneath the breast and, as will be appreciated from FIG. 8, extend inwardly a short distance therebeneath. As will be further appreciated from FIGS. 2 and 8, outer edge 50d of panel 50 extends laterally outwardly and generally across the center of the patient's breast from bottom edge 50b to top edge 50a. During pulling of dressing halves 14 and 16 across the chest to engage Velcro fastener components 30 and 46, the corners of panels 34 and 50 formed by the top and outer edges thereof compress the patient's flesh in the area near the corresponding armpit toward the patient's front to prevent any uncomfortable rubbing or chafing. As dressing halves 14 and 16 are pulled toward the patient's front, panels 34 and 50 engage the outerside and underside of the corresponding breast to support and push it in the direction of arrow B in FIGS. 3, 8 and 10 toward incision 88. As will be further appreciated from these figures, the shape of non-stretchable panels 34 and 50 allows the panels to provide the greatest amount of support and bias for the patient's breasts without constricting other parts of a patient's back, breasts or sides. When dressing 10 is properly positioned, inner edges 34c and 50c of panels 34 and 50 slope downwardly and inwardly from the patient's armpit areas, as shown in FIGS. 2 and 8, to prevent any uncomfortable restriction of the patient's flesh on the patient's sides. Inner edges 34c and 50c begin near the location where the patient's corresponding arm meets the patient's front and extends downwardly and inwardly toward incision 88 to bottom elastic strip 68. Being so shaped, non-stretchable panels 34 and 50 lift and bias the patient's breasts away from the patient's sides while the stretchable material in other areas of the right and left dressing halves where less support is needed provides for maximum comfort. This differential support both speeds healing and maximizes comfort.

As will be appreciated from FIGS. 2 and 3, stays 38 and 56 are located along the sides of the patient beneath the patient's armpits. These stays help to support the portions of dressing 10 along the patient's sides and to keep dressing 10 flat against the patient's body. Without these stays, dressing 10 could roll or bunch beneath the patient's arms. Such bunching is not only uncomfortable, but also alters the tension placed on incision 88 by dressing 10. If dressing 10 is too tight across some portions of incision 88 and not tight enough across others, unnecessary stresses will be placed on the incision, interfering with the healing process. By keeping dressing 10 flat against the patient's body, stays 38 and 56 help maintain an even pressure across the patient's chest and across incision 88 therein.

Stays 38 and 56 are positioned across the width of dressing 10 so that end 38a of stay 38 is closer to stretchable panel 12 than is end 38b of stay 38 and such that end 56a of stay 56 is positioned closer to stay 56 than is end 56b. In this manner, as best seen with respect to stay 56 in FIG. 2, when dressing 10 is placed on a patient, end 56a is closer to horizontal surface 51 than is end 56b. A stay not angled in this manner tends to poke a patient in the side. By angling the stays so that end 56b is closer to the patient's chest, stay 56 tends to slide against the patient's side as the patient breathes, instead of poking the patient. In the preferred embodiment, end 56a is offset approximately ¾ inches from end 56b.

The invention has been described with reference to preferred embodiments and it is apparent that other embodiments, as well as modifications of the preferred embodiments can be made without departing from the principles of the invention. Accordingly, it will be distinctly understood that the foregoing descriptive matter is to be interpreted merely as illustrative of the invention and not as a limitation.

Having thus described the invention, it is claimed:

1. A surgical chest dressing comprising:
   a chest encircling flexible band formed primarily from a stretchable material and having free ends overlapping each other at engaging surfaces generally centrally of the chest of a person about which the dressing has been wrapped; and
   said band including first and second non-stretchable support panel means for biasing body tissue of said person therebeneath in a desired direction relative to the person's chest, wherein said first and second non-stretchable support panel means are separated by a first section of stretchable material and spaced apart from each of said free ends by second sections of stretchable material.

2. A surgical chest dressing according to claim 1, wherein said non-stretchable support panel means overlies a portion of at least one side of said person and the adjacent side area of said person's breast.

3. A surgical chest dressing according to claim 1, wherein said non-stretchable support panel means comprises first and second non-stretchable support panel means.

4. A surgical chest dressing according to claim 3, wherein said first non-stretchable support panel means overlies the side and breast tissue on one side of the person's chest and said second non-stretchable support panel means overlies the side and breast tissue on the opposite side of the person's chest.

5. A surgical chest dressing according to claim 4, wherein the side and breast tissue beneath said first and second non-stretchable support panel means are biased toward one another.

6. A surgical chest dressing according to claim 3, wherein said first non-stretchable support panel means comprises a first panel of non-stretchable material attached to said band of stretchable material and said second non-stretchable support panel means comprises a second panel of non-stretchable material attached to said band of stretchable material.

7. A surgical chest dressing according to claim 1, including stiffening means to prevent said stretchable material of said band from folding transverse to the direction between said free ends along said person's sides.

8. A surgical chest dressing according to claim 7, wherein said stiffening means comprises at least one strip member of flexible material attached to said band to extend transverse to said direction.

9. A surgical chest dressing according to claim 5, wherein said band includes an elastic panel overlying said person's back.

10. A surgical chest dressing according to claim 9, wherein said band includes upper and lower edges between said ends, an upper band of elastic material attached to said upper edge, and a lower band of elastic material attached to said lower edge.

11. A surgical chest dressing according to claim 1, including strip means for maintaining an even closing pressure around said person's chest.

12. A chest encircling surgical dressing comprising band means of stretchable material having free ends, and a pair of panels of non-stretchable material attached to said band means for biasing the breast tissue of a person wearing said dressing inwardly of said person's chest, wherein said pair of non-stretchable panels is separated from each of said free ends by at least one section of stretchable material.

13. A surgical dressing according to claim 12, wherein said panels substantially immobilize the breast tissue of said person.

14. A surgical dressing according to claim 13, wherein said band means includes an elastic panel for enabling said band means to expand and contract as said person breathes.

15. A surgical dressing according to claim 12, wherein said non-stretchable panels bias the side tissue of said person adjacent said breast tissue inwardly of said person's chest and bias said side and said breast tissue differentially.

16. A surgical dressing according to claim 15, wherein said bias is greatest adjacent said person's armpits and decreases along said person's sides in the direction downwardly from said armpit.

17. A surgical dressing according to claim 16, wherein said band means includes stay means for supporting said band means against flexing.

18. A surgical dressing according to claim 17, wherein said stay means comprises strip member means attached to said band means, said strip member means being of a material less flexible than the material of said band means.

19. A surgical dressing according to claim 12, wherein said band means comprises two plys of stretchable material fastened together, said panels of non-stretchable material being disposed therebetween.

20. A surgical dressing according to claim 12, including strip means attached to said band means for maintaining an even closing pressure about the chest of said person.

21. A surgical chest dressing comprising elongate band means of stretchable material having a first end and a second end, and first and second interengagable fastening means respectively on said first and second ends of said band means, said band means including spaced apart edges extending between said first and second ends, said edges providing for said band means to have a first width in a central portion of said band means between said ends and a second width between said first and second ends of said band means respectively between said central portion and said first end and between said central portion and said second end, said second width being greater than said first width, said central portion of said band means including an elastic panel, a first non-stretchable panel supported on a first portion of said band means between and spaced apart from said elastic panel and said first fastening means, and a second non-stretchable panel supported on a second portion of said panel means between and spaced apart from said elastic panel and said second fastening means.

22. A surgical chest dressing according to claim 21, further including stay means between said spaced apart edges of said first and second portions of said band, said stay means being between each of said first and second non-stretchable panels and said elastic panel.

23. A surgical chest dressing according to claim 22, wherein said first and second fastening means comprise interengaging loop and hook components.

24. A surgical chest dressing according to claim 23, wherein said stay means comprise strip member means less flexible than the material of said band means.

* * * * *